(12) United States Patent
Hirose et al.

(10) Patent No.: US 8,279,431 B2
(45) Date of Patent: Oct. 2, 2012

(54) SPECTRAL DETECTION METHOD AND DEVICE, AND DEFECT INSPECTION METHOD AND APPARATUS USING THE SAME

(75) Inventors: Takenori Hirose, Yokohama (JP); Minoru Yoshida, Yokohama (JP); Hideaki Sasazawa, Yokohama (JP); Yasuhiro Yoshitake, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 486 days.

(21) Appl. No.: 12/626,963

(22) Filed: Nov. 30, 2009

(65) Prior Publication Data

US 2010/0182589 A1  Jul. 22, 2010

(30) Foreign Application Priority Data

Jan. 16, 2009 (JP) ................. 2009-007160

(51) Int. Cl.
*G01N 21/00* (2006.01)
(52) U.S. Cl. ............... 356/237.1; 356/237.2; 356/237.4
(58) Field of Classification Search .... 356/237.1–241.6, 356/242.1–243.8, 426–431, 600–640
See application file for complete search history.

(56) References Cited

U.S. PATENT DOCUMENTS

| | | | | |
|---|---|---|---|---|
| 4,391,524 A | * | 7/1983 | Steigmeier et al. | 356/338 |
| 5,548,401 A | * | 8/1996 | Ozaki | 356/239.3 |
| 6,532,067 B1 | * | 3/2003 | Chang et al. | 356/318 |
| 6,734,967 B1 | * | 5/2004 | Piwonka-Corle et al. | 356/369 |

FOREIGN PATENT DOCUMENTS

| | | |
|---|---|---|
| JP | 2007-285761 | 11/2007 |
| JP | 2009-150832 | 7/2009 |

* cited by examiner

*Primary Examiner* — Gregory J Toatley
*Assistant Examiner* — Jarreas C Underwood
(74) *Attorney, Agent, or Firm* — Antonelli, Terry, Stout & Kraus, LLP.

(57) ABSTRACT

In spectral detection for detecting the shape of repeating pattern structures uniformly formed on a surface of a test object, it is advantageous to use light having a wide wavelength range in a short wavelength region. However, it is not easy to realize a relatively simple optical system capable of spectral detection of light having a wide wavelength range in a short wavelength region, namely in ultraviolet region. The present invention provides an inspection apparatus for detecting pattern defects. The inspection apparatus includes a spectral detection optical system capable of spectral detection of light in a wavelength range from deep ultraviolet to near infrared. The spectral detection optical system includes a spatially partial mirror serving as a half mirror and a reflecting objective provided with an aperture stop for limiting the angle and direction of light to be applied to and reflected by a test object.

12 Claims, 16 Drawing Sheets

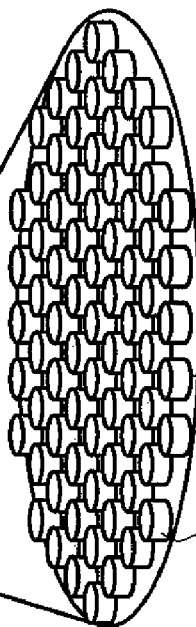
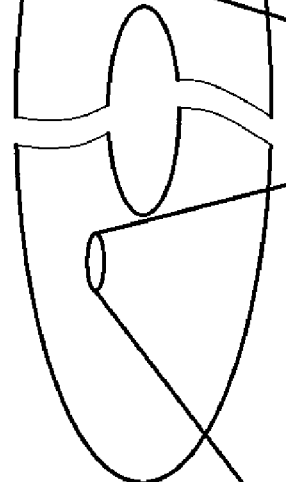
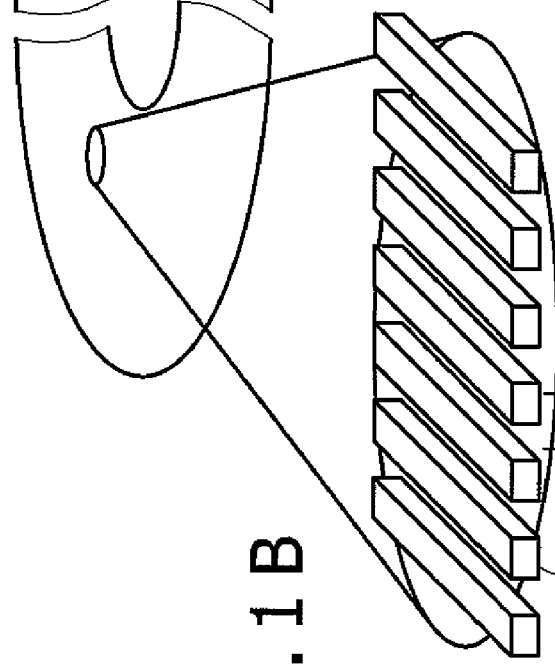

SPECTRAL DETECTION METHOD AND DEVICE, AND DEFECT INSPECTION METHOD AND APPARATUS USING THE SAME

BACKGROUND OF THE INVENTION

1. Field of the Invention

The present invention relates to optical systems capable of spectral detection of light in a wide wavelength range from deep ultraviolet to near infrared. The present invention also relates to inspection apparatuses for inspecting, together with the optical systems, a test object having minute repeating pattern structures of several tens of nanometers in size formed on its substrate, namely patterned media such as semiconductor devices and next-generation hard disk media, in order to optically detect the shape of the pattern structures and whether the pattern structures are properly formed.

2. Description of the Related Art

There has been an ever-growing trend over the years to increase the storage capacity of hard disk drives more. However, conventional substrate disks with a magnetic film formed thereon, or equivalently, so-called continuous media, have a storage density, at its greatest, of approximately 1 Tbit/in$^2$, which is deemed to be their limit. Instead of the continuous media, planned to be introduced are patterned media as a technique for achieving higher storage densities than 1 Tbit/in$^2$.

Patterned media are classified into two types: discrete track media, as shown in FIG. 1B, having recording tracks 0102 with grooves formed therebetween on a disk 0101 shown in FIG. 1A; and bit-patterned media, as shown in FIG. 1C, having isolated islands 0103 each corresponding to a unit of recording (a bit). Unlike conventional continuous media, both patterned media are characterized in that the patterns are formed on a disk medium (substrate) so as to arrange the identically-shaped tracks or islands (pattern structures) at a pitch of tens of nanometers.

The patterned media require an additional new manufacturing process for patterning, which arouses a concern for defects caused by the process. FIG. 2, which is a schematic diagram of the cross sectional profile of the pattern, shows proper pattern structures 0201 and possible defects, for example, deformed pattern structures 0202 and an area lacking the pattern structures 0203.

Measures to inspect defects in these minute pattern structures include an optical inspection method, or so-called scatterometry, in addition to direct observation measures, such as atomic force microscopes (AFM) and scanning electron microscopes (SEM). The AFM, SEM and scatterometry are well known techniques in this technical field. In comparison with the AFM and SEM, scatterometry that utilizes an optical method can conduct faster inspections.

Scatterometry is generally a technique, as shown in FIG. 3, in which a spectral detection optical system 0301 detects a spectral reflectance 0303 of a surface of a test object 0302 to detect the shape of the repeating pattern structures 0304 uniformly formed on the surface of the test object 0302 based on the detected spectral reflectance 0303. If the uniformly formed pattern has a cross-sectionally deformed pattern structure, the structure exhibits a different spectral reflectance. Utilizing this phenomenon, the shape of the pattern uniformly formed on the surface of the test object can be detected by the spectral reflectance. The shape detection also uses some other techniques such as a model fitting approach and library matching approach.

It is known that this technique can perform the shape detection with higher sensitivity when the detected light covers a wider range in a short wavelength region.

The shape detection, by scatterometry, of the pattern uniformly formed on the test object surface can be advantageously made with light covering a wide wavelength range in a short wavelength region. However, it is not easy to realize an optical system capable of the spectral detection with light in a wide wavelength range including short wavelengths, that is, an ultraviolet range. Even if possible, such an optical system will be very expensive.

The optical system includes optical elements each having limited wavelength characteristics. Especially, among the optical elements, most half mirrors are not suitable for light having the wide wavelength range from ultraviolet to infrared. Even if there is a suitable half mirror, it will cost a lot.

JP-A No. 285761/2007 discloses one example of methods for realizing relatively inexpensive half mirrors available for light from the ultraviolet to infrared range.

SUMMARY OF THE INVENTION

When the spectral detection optical system used in scatterometry is assembled with the same components as a general optical microscope, the numerical aperture (NA) of an objective limits the angle ranges of light irradiated to the surface of a test object and reflected light from the surface of the test object. In addition, the light is applied from every direction from 0 to 360 degrees. Because of this, the detected spectral data contain information of light irradiated and detected in various directions and at various angles, which complicates analysis for detecting the shape and defects of the pattern based on the spectral data.

The present invention adopts a spatially partial mirror instead of the half mirror and an objective incorporating an aperture stop that limits the angle and direction of light applied to the test object and light reflected from the test object to be detected, thereby realizing a spectral detection optical system capable of detecting light having wavelengths from deep ultraviolet to near infrared.

In the present invention, a defect inspection apparatus includes a stage unit on which a sample is placed, a spectral detection optical unit spectrally detecting reflect light, the reflected light being light that is applied to the sample on the stage unit is reflected by the sample, a data processing unit detecting the shape and defects of the sample on the stage unit based on results of the spectral detection performed by the spectral detection optical unit, and a stage control unit controlling the movement of the stage unit. The spectral detection optical unit includes a light source emitting light in a wavelength range including ultraviolet, an optical path switcher having a light-transmitting section and a light-reflecting section. The optical path switcher switches an optical path of the light emitted from the light source by reflecting the light with the light-reflecting section. The spectral detection optical unit also includes a reflecting objective focusing the light whose optical path has been switched by the optical path switcher onto a surface of the sample, and a spectral detector subjecting reflected light to spectral detection, the reflected light being the light that is applied onto the surface of the sample by the reflecting objective, is reflected by the sample surface, passes through the reflecting objective and the light-transmitting section of the optical path switcher.

The present invention can provide an optical system capable of spectral detection of light covering a wide wavelength range from deep ultraviolet to near infrared with relatively simple components. The optical system makes it possible to detect the shape and defects of a pattern on a sample, the pattern being made of multiple minute repeating pattern structures of approximately several tens of nanometers in size, for example.

BRIEF DESCRIPTION OF THE DRAWINGS

Embodiments of the present invention will be described in detail based on the following figures, wherein:

FIGS. 1A to 1C are perspective views illustrating examples of patterned media;

DETAILED DESCRIPTION OF THE INVENTION

Figure 2:
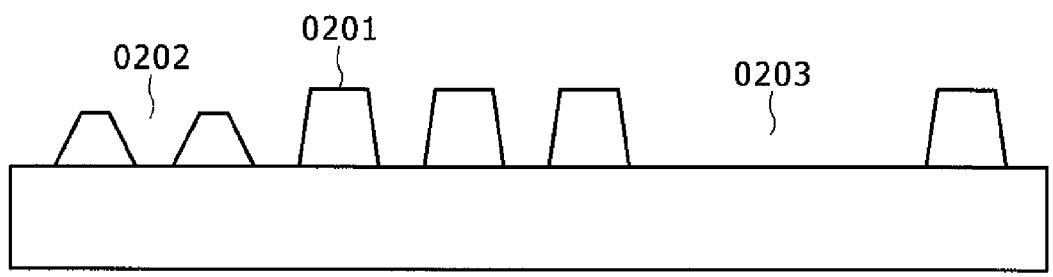
FIG. 2 is a cross-sectional view of a patterned medium to indicate exemplary defects thereof.
Figure 3:
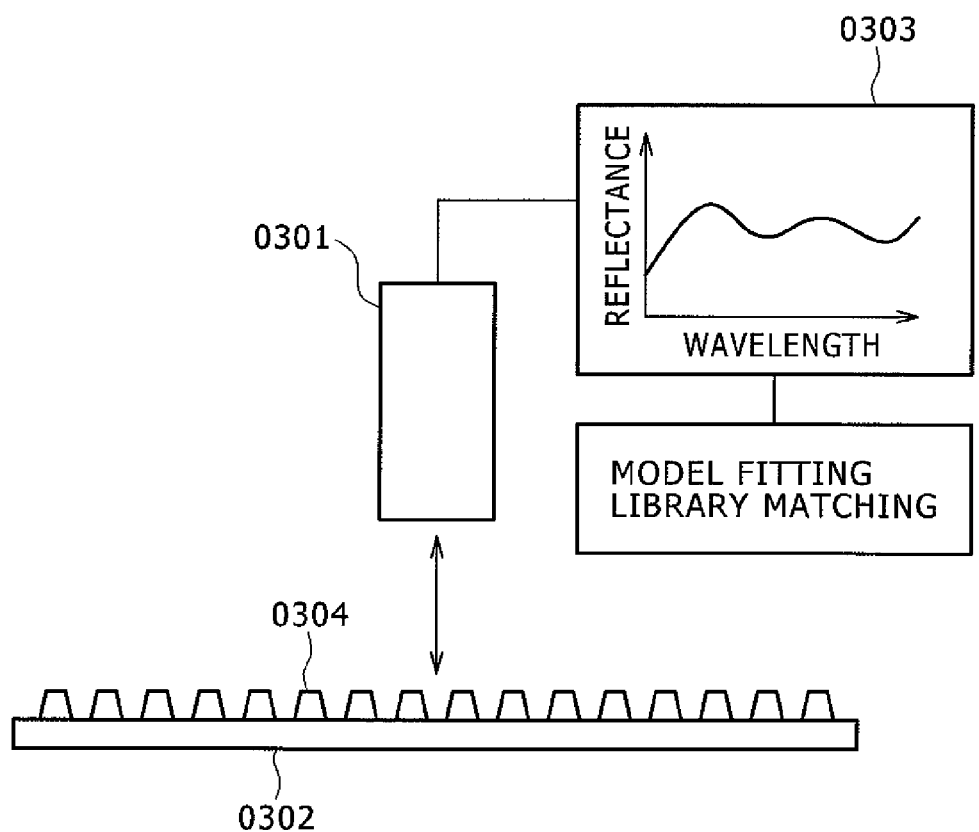
FIG. 3 is a block diagram illustrating conventional scatterometry.

The present invention will be first described with an exemplary method for optically detecting the shape of a pattern formed on a disk. FIG. 1 shows a patterned medium mainly intended for the present invention, the patterned medium having pattern structures, each of which is approximately tens of nanometers in size, repeatedly formed on a disk. If the height or with of a pattern structure is changed, so is the spectral reflectance of the entire surface on which the pattern structures are formed. In short, a different pattern shape results in a different spectral reflectance. Because of this, detection of the spectral reflectance of an object surface allows the shape of the object pattern to be detected.

One of such methods for detecting the shape of repeating minute pattern structures is scatterometry. With an electromagnetic-wave analysis technique, such as a rigorous coupled-wave analysis (RCWA), the spectral reflectance of the test object surface can be obtained from optical constants of the shape and materials of the pattern structures. The reflectances of the test object surfaces are calculated in advance using various parameters, which are values representing the shape of a pattern structure, such as a height and width. Then, the calculated reflectances are compared with an actually detected surface reflectance to extract the reflectance closest to the actually detected reflectance, whereby the shape of the pattern structures of the object can be detected. Alternatively, the reflectance calculated with the use of the RCWA is fitted into the actually detected reflectance with values representing pattern shapes such as height and widths as parameters (fitting operation), whereby particular pattern shapes can be detected.

The other method uses an effective medium approximation to detect the shape of an object pattern. First, the effective medium approximation will be explained using a case where a test object includes two media a (pattern) and b (air). In this case, if the area size of each medium is smaller than or equal to about one tenth of a wavelength of light used for detection, it is no longer necessary for the medium a and medium b to be distinguished from each other, but can be treated as one layer. When dielectric constants of the media a and b are $\epsilon_a$ and $\epsilon_b$), respectively, and the occupation ratio of a pattern is $f_a$, the dielectric constant $\epsilon_c$ of the approximate layer is expressed by Equation 1.

As described above, the approximation of a layer, which is formed of multiple media, as a single medium layer is referred to as "effective medium approximation". Equation 1 used to explain the effective medium approximation is merely an example, and an optimal equation is necessarily selected based on the shape and material of the object.

[Equation 1]

$$\epsilon_c = \frac{\epsilon_a \epsilon_b + \chi \epsilon_h (f_a \epsilon_a + f_b \epsilon_b)}{\chi \epsilon_h + (f_a \epsilon_b + f_b \epsilon_a)} \quad \text{Eq. 1}$$

$$\chi = (1-q)/q$$

$\epsilon_a$, $\epsilon_b$, $\epsilon_c$: complex dielectric constants
$f_a$: occupation ratio
$\chi$: shielding factor In a case where the test object includes a monolayer film and the refractive index n and extinction coefficient k of the film and its base are known, the spectral reflectance of the film surface can be given by Fresnel's formula shown as Equation 2. The film thickness of the test object can be determined by fitting the reflectance obtained by Fresnel's formula into an actually detected spectral reflectance with the film thickness as a parameter (fitting operation).

[Equation 2]

$$|R|^2 = \left| \frac{r_2 + r_1 e^{-2ni 2d_3 \frac{n-ik}{\lambda}}}{1 + r_1 r_2 e^{-2ni 2d_3 \frac{n-ik}{\lambda}}} \right| \quad \text{Eq. 2}$$

$$rq = \frac{(n_q - ik_q) - (n_{q-1} - ik_{q-1})}{(n_q - ik_q) + (n_{q-1} - ik_{q-1})}$$

n: refractive index
k: extinction coefficient
d: film thickness
$\lambda$: wavelength $r_1, r_2$: boundary reflectances between a base and a film and the film and air The refractive index n, extinction coefficient k and dielectric constant establish the relationship expressed by Equation 3, and therefore the fitting operation for determining film thickness can be used for the films that have been subjected to the effective medium approximation. Even though the occupation ratio $f_a$ is not known at the time of the effective medium approximation, the occupation ratio can be concurrently obtained by treating the occupation ratio as a parameter upon the fitting operation.

[Equation 3]

$$\epsilon = \epsilon_1 - i\epsilon_2$$

$$\epsilon_1 = n^2 + k^2$$

$$\epsilon_2 = 2nk \qquad \text{Eq. 3}$$

ε: complex dielectric constant
n: refractive index
k: extinction coefficient

The foregoing describes a method for detecting the shape of the pattern formed on a disk based on the reflectance of the disk surface. However, in the actual product inspection, the shape detection may not always necessary item to be tested. Some product inspections are expected to only judge whether the object is non-defective or not.

Next, a method for determining only whether the object is non-defective or not will be described.

The difference in shape of the pattern structures makes difference in spectral reflectance of the surface of the pattern. Suppose, among two pattern groups that have been originally planned to be identical in shape, one of the pattern groups has a normal spectrum waveform, the other pattern group can be determined to be abnormal by detecting a difference in spectrum waveform of the other pattern group.

The difference in spectral reflectance is detected with a determination index value Delta as shown in Equation 4. The determination index value Delta represents the difference between a reference waveform and a detected waveform. The determination whether the pattern shape is abnormal or not can be made by comparing the determination index value with a predetermined threshold value. Specifically, if the determination index value is equal to or greater than the threshold value, the pattern is determined to be defective, whereas if it is smaller than the threshold value, the pattern is determined to be non-defective.

[Equation 4]

$$\text{Delta} = \sqrt{\Sigma\{R_{Standard}(\lambda) - R(\lambda)\}^2} \qquad \text{Eq. 4}$$

$R_{standard}$: spectral reflectance of normal pattern
R: detected spectral reflectance
λ: wavelength An example of the methods for setting the threshold value used for determination includes: collecting spectral reflectances of patterns having various widths and heights; obtaining determination index values from the spectral reflectances of patterns to be determined normal and determination index values from the spectral reflectances of patterns to be determined abnormal; and setting a threshold value so as to separate the normal patterns and abnormal patterns. The threshold value draws a distinction between the determination index values of the spectral reflectances to be determined normal and the determination index values of the spectral reflectances to be determined abnormal, thereby separating normal patterns from abnormal patterns.

It is preferable to use the actually detected spectral reflectances for setting the threshold value; however, spectral reflectances obtained through optical simulations can be also used.

It is found that light having a wavelength of 400 nm or less (i.e., ultraviolet rays) greatly varies its reflectance in comparison with light having a wavelength exceeding 400 nm. This indicates that detecting light in the ultraviolet region to obtain the spectral reflectances is advantageous from the viewpoint of the sensitivity required to detect the shapes and defects.

Under normal conditions, detectable wavelength of light in the atmosphere is down to approximately 200 nm. In practice, it is realistic to detect light having a wavelength of 200 nm or more. Of course, detection of light in a wavelength range of 200 nm or less improves the sensitivity for detecting the shapes and defects.

The following are descriptions about a structure for detecting a spectral reflectance of the surface of a test object, the spectral reflectance being required to detect the shape and defects of the pattern on the object, and a structure of a defect inspection apparatus including a unit for detecting the spectral reflectance.

Embodiment 1

Figure 4:
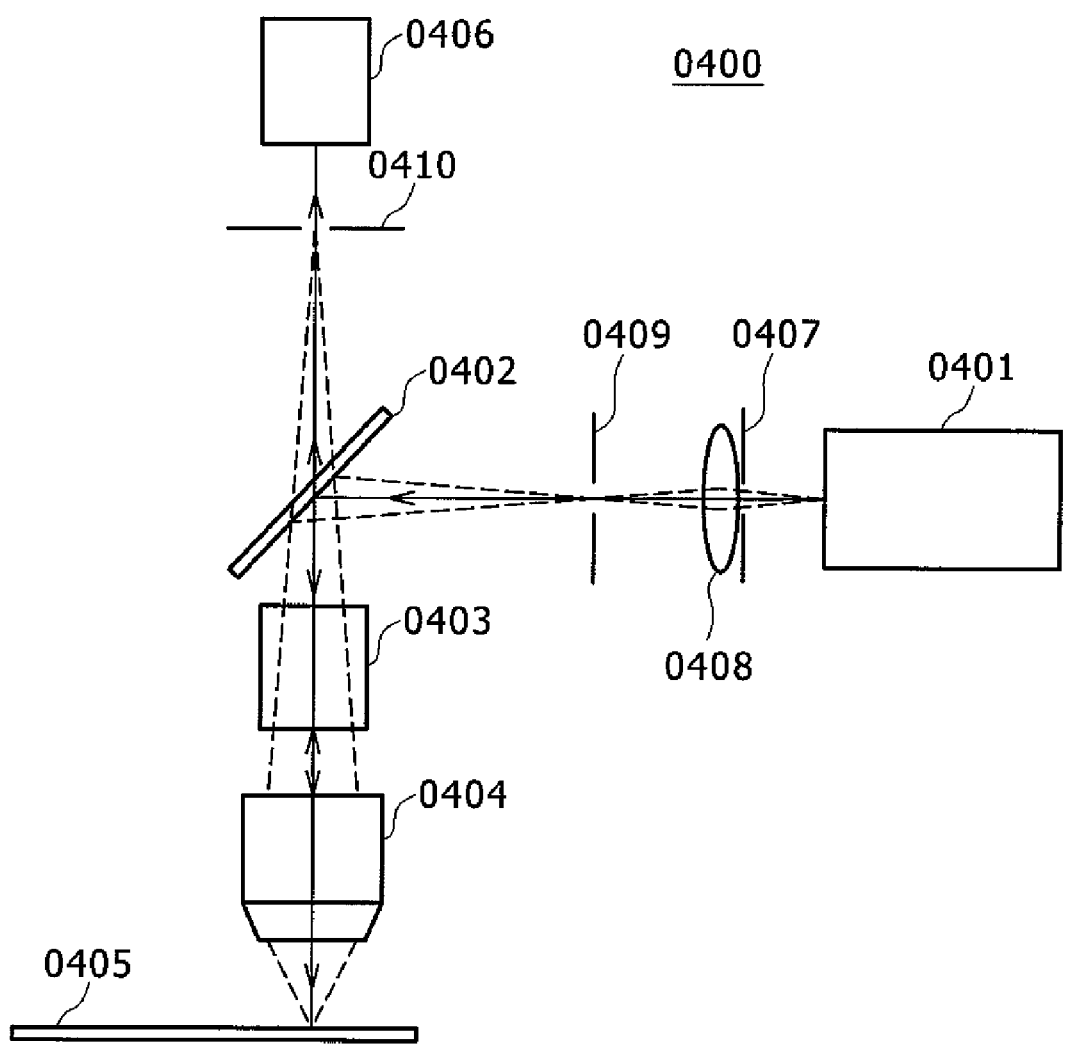
FIG. 4 is a front view illustrating the basic structure of a spectral detection optical system according to Embodiments 1 and 2.

FIG. 4 shows an example of a spectral detection optical system 0400 realized with an optical microscope. Light emitted from a light source 0401 passes through an aperture of a first diaphragm 0407, is focused by a condenser lens 0408, passes through an aperture of a second diaphragm 0409, is reflected by a half mirror 0402 to change the direction, and is irradiated on a sample surface 0405 via a polarizing element 0403 and an objective 0404. Subsequently, the light is reflected on the sample surface 0405, passes through the objective 0404 and polarizing element 0403 again, and the half mirror 0402. An aperture of a third diaphragm 0410 allows the light to pass therethrough in order to shield disturbance light and introduce only the light reflected by the sample surface 0405 to a spectral detector 0406.

For spectrally detecting light in a wavelength range from deep ultraviolet to near infrared, all of the above-described components in the optical system need to be usable for the light in the wavelength range.

The light source 0401 may be a xenon lamp or a deuterium lamp that can emit light in a wavelength range from around 190 nm to near infrared. As to the objective 0404, general refractive-type objectives seldom allow the light in a wavelength range from deep ultraviolet to near infrared to pass therethrough and are not applicable for light having a broad wavelength range because the objectives create great chromatic aberration caused by wavelength dispersion derived from their refractive index. To overcome the drawbacks, reflecting objectives made of a mirror have been developed. Although it depends on the material and surface coating, general mirrors made of aluminum or the like can reflect light in a wide wavelength range, and their surfaces, such as a spherical surface, are designed to reflect and focus light so as not to create chromatic aberration. In this embodiment, the reflecting objective is adopted as the objective 0404.

As to the spectral detector 0406 and polarizing element 0403, those components usable with light in a wide wavelength range from ultraviolet to near infrared (190 nm to 800 nm) are nowadays readily available. The polarizing element has properties of polarizing non-polarized light into linearly-polarized light.

However, as to the half mirror 0402, there are few half mirrors usable with light in a broad wavelength range from deep ultraviolet to near infrared. Even if there were one, such a half mirror is very expensive.

Figure 5:
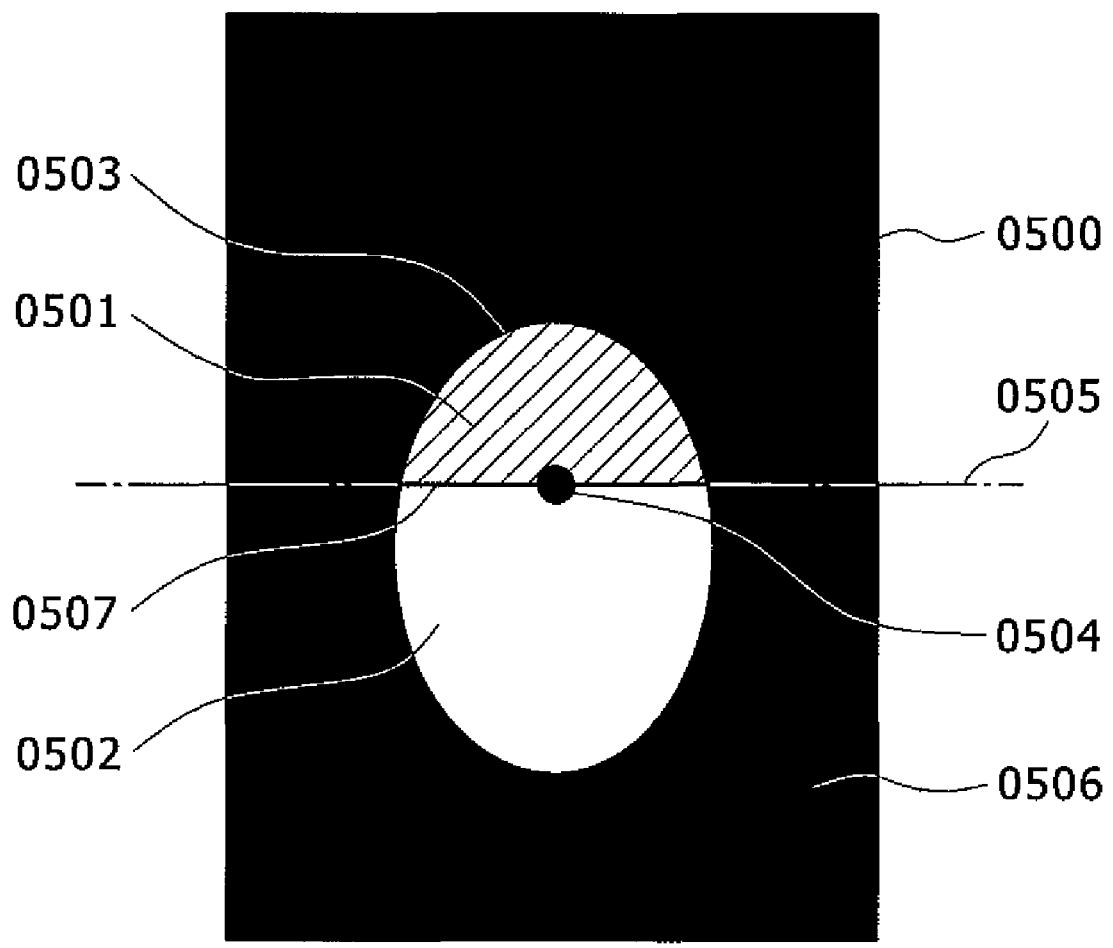
FIG. 5 is a plan view illustrating an example of a half mirror.

In this invention, instead of the half mirror 0402, a spatially partial mirror 0500 as shown in FIG. 5 is used to realize an optical system capable of spectrally detecting light in a wavelength range from deep ultraviolet to near infrared. This mirror can be easily made by arranging a mirror on a part of a glass substrate or making a hole in a mirror.

FIG. 5 shows an example of the spatially partial mirror 0500 provided with only a single part through which light can pass. In this example, a part of light from the light source 0401 is reflected by a mirror section 0501 but the other part of the light passes through a non-mirror section 0502 to go out of the optical system. The light reflected by mirror section 0501 is irradiated on the sample surface 0405 via the objective 0404, and the light reflected by the sample surface 0405 enters again the objective 0404 to reach the spatially partial mirror 0500. The mirror section 0501 and non-mirror section 0502 are optimally shaped and arranged so that most parts of light, which has been reflected by the mirror section 0501 and irradiated onto and reflected by the sample surface 0405, can pass through the non-mirror section 0502, thereby realizing an efficient optical system. The light having passed through the non-mirror section 0502 and polarizing element 0403 is detected by the spectral detector 0406.

In the case of the so-called finite optical system as shown in FIG. 4, light is set to impinge onto an ellipse part 0503 in FIG. 5. The mirror section 0501 and non-mirror section 0502 are defined by a boundary, or namely a straight line 0505, which is parallel to an ellipse's minor axis and lies over a focal point of the ellipse, thereby realizing the efficient optical system. In the case of FIG. 5, the area 0506 outside the ellipse part 0503 shields light.

The optical system adopting the spatially partial mirror 0500 instead of the half mirror 0402 is, in fact, separated into an illumination system and a detection system.

Figure 6:
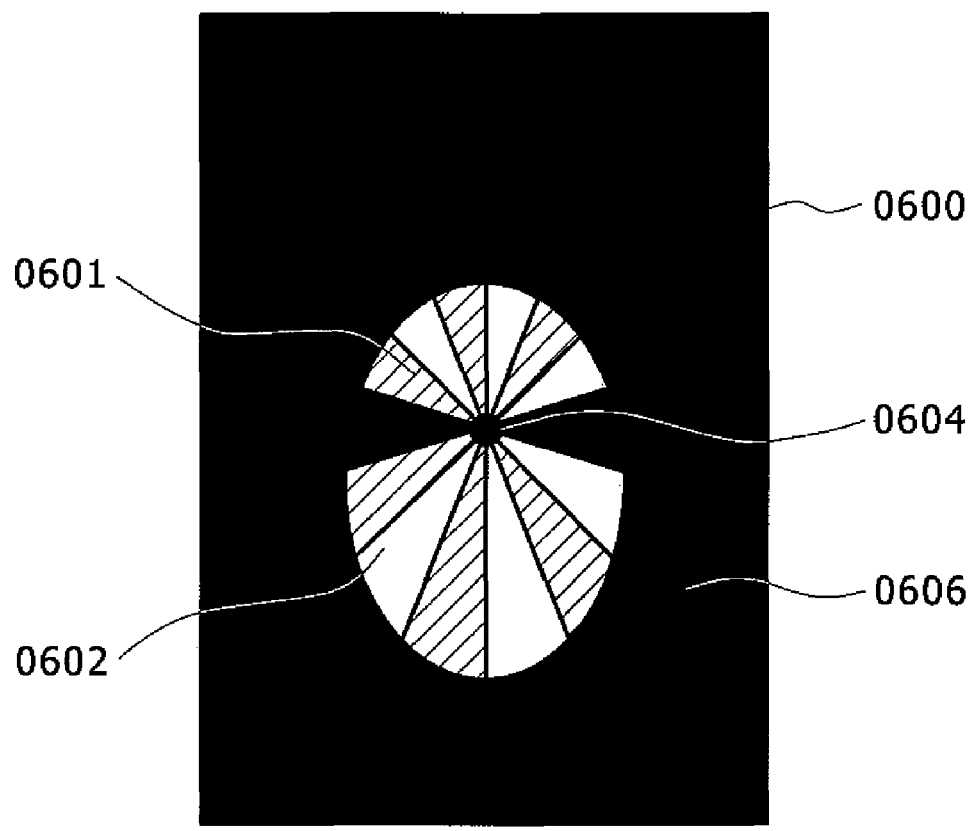
FIG. 6 is a plan view illustrating another example of the half mirror.
Figure 7:
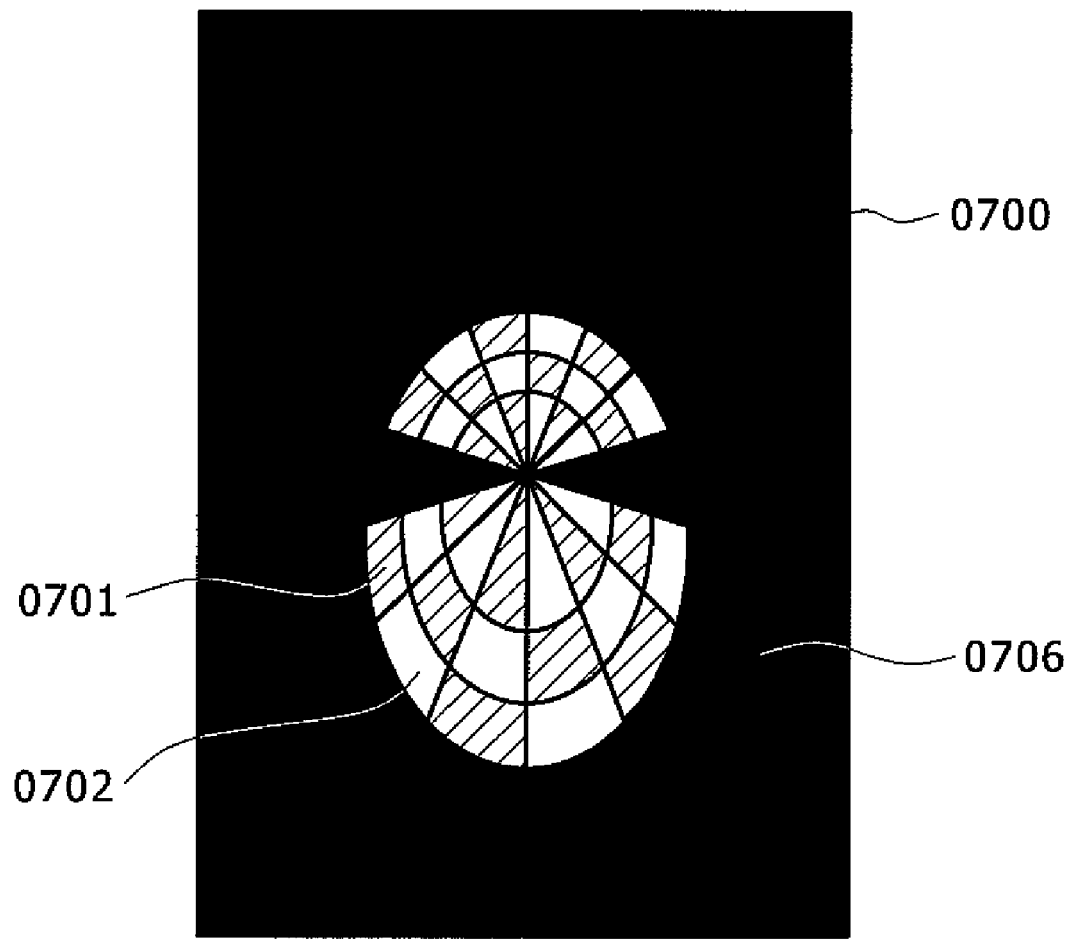
FIG. 7 is a plan view illustrating yet another example of the half mirror.

Other examples of the half mirror 0402 may include spatially partial mirrors 0600 and 0700, as shown in FIG. 6 and FIG. 7, respectively, those of which are modifications of the mirror in FIG. 5.

The mirror in FIG. 6 has radially disposed mirror sections 0601 and non-mirror sections 0602, while the mirror in FIG. 7 has mirror sections 0701 and non-mirror sections 0702 which are alternately arranged in segments formed by radially dividing multiple ellipses which share a focal point. Both of the mirrors 0600 and 0700 are placed so that light reflected by the mirror sections 0601 or 0701 and returned from a sample passes through the non-mirror sections 0602 or 0702.

In principle, in a pair of segments with respect to an optical axis (one of the focal points of the ellipse), one segment is applied to the mirror section 0501, 0601 or 0701, and the other segment is applied to a non-mirror section 0502, 0602 or 0702, thereby obtaining the aforementioned effect.

Above described JP-A No. 285761/2007 discloses that the mirror section and non-mirror section are symmetric with respect to a point. On the other hand, according to the present invention, light strikes the ellipse part (0503 in FIG. 5), and the optical axis is designed to lie over one of the focal points of the ellipse. In other words, the mirror sections 0501, 0601, 0701 and the non-mirror sections 0502, 0602, 0702 paired up therewith in the present invention are not symmetric in shape with respect to a point.

Finite optical systems do not require additional optical elements for forming images upon spectral detection performed with deep ultraviolet light, which means the finite optical systems are advantageous in the reduction of aberrations and have fewer components. The thus shaped spatially partial mirrors are applicable to the finite optical systems.

In addition, JP-A No. 285761/2007 also discloses that the numbers of mirror sections and non-mirror sections are odd, respectively. To use the entire area of the ellipse (0503 in FIG. 5) on which light impinges, the numbers of the mirror section 0501 and non-mirror section 0502 must be odd, respectively. However, an aperture stop, which will be described later, eliminates the necessity to always use the entire area of the ellipse and, therefore, as shown in FIG. 6 and FIG. 7, the mirror sections 0601, 0701 and non-mirror sections 0602, 0702 can be set to an even number.

The even number of the mirror sections and the non-mirror sections allows light having symmetric angular components to be irradiated to the test object, thereby reducing the calculation burden for spectroscopic data analysis.

The ellipse part separated into two sections, i.e., a mirror section 0501 and a non-mirror section 0502 as shown in FIG. 5 deflects the light traveling to the sample to one side; however, separating the mirror section 0501 and non-mirror section 0502 into smaller sections makes it possible to apply the light and detect the light in various directions.

If the separated sections are uniformly arranged, the repeatedly arranged mirror and non-mirror sections may cause diffraction which requires careful consideration. An evaluation as to how much the diffraction affects light on a sample surface 0405 and at a spectral detection position can be made based on the repeating pitch of the mirror sections or non-mirror sections and the specification of the objective. It is desirable to design the mirror so as not to detect diffracted light on the sample surface and at spectral detection position.

Figure 16:
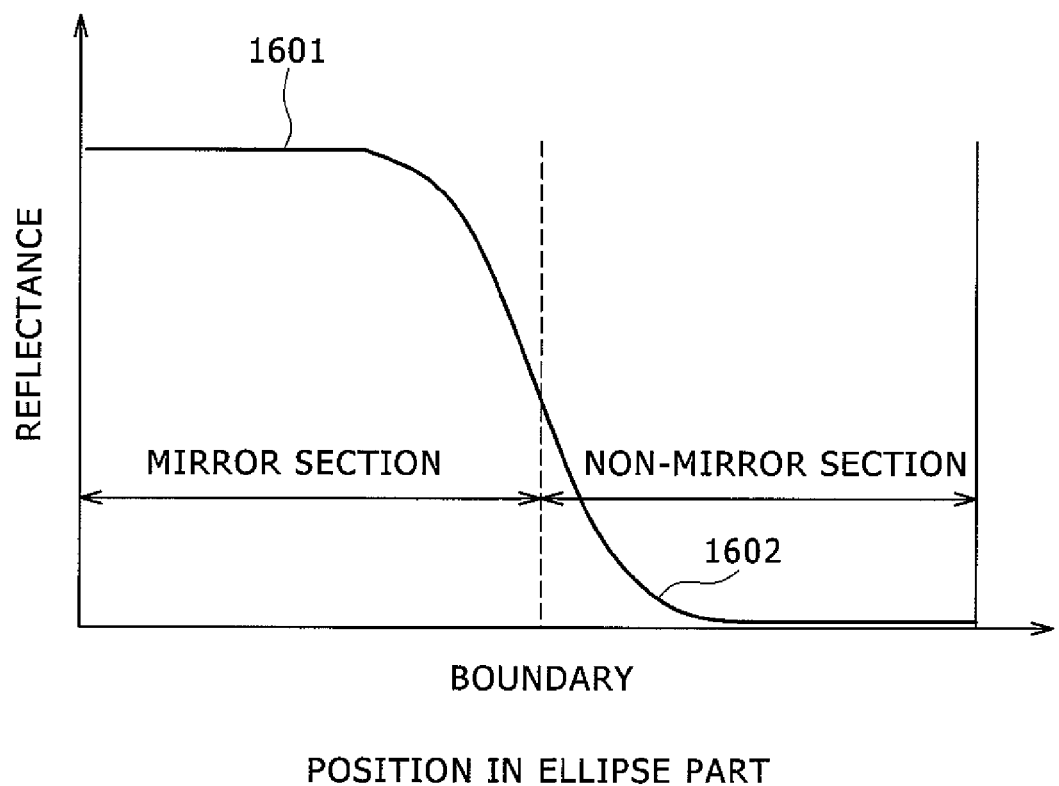
FIG. 16 is a graph showing reflectances of a mirror section and non-mirror section in a half mirror.

Even though the separated sections do not appear repeatedly as shown in FIG. 5, light is diffracted at the boundary 0507 between the mirror section 0501 and non-mirror section 0502, and the diffracted light that is detected by the spectral detector 0406 at last causes an error. The occurrence of the diffraction can be decreased by seamlessly varying the reflectance at the boundary between the reflectance 1601 of the mirror section and the reflectance 1602 of the non-mirror section as shown in FIG. 16.

Figure 8:
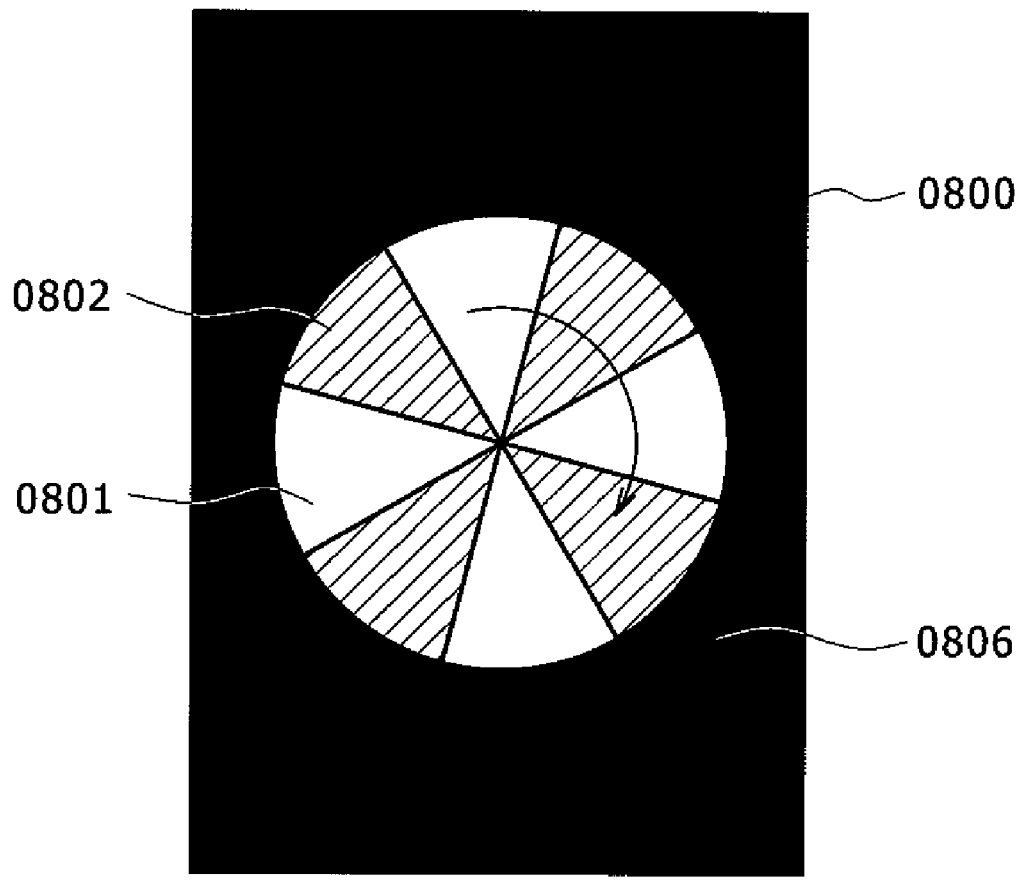
FIG. 8 is a plan view illustrating yet another example of the half mirror.

It is also conceivable to spin a spatially partial mirror 0800 in FIG. 8 (the arrow in FIG. 8 indicates rotational movement). This mirror 0800 rotates to change the position of mirror sections 0801, whereby light emitted toward the sample surface 0405 is deflected and light reflected by the sample surface 0405 and passing through the non-mirror sections 0802 is detected by the spectral detector 0406 after passing through the polarizing element 0403. Therefore, the mirror 0800 enables illumination and spectral detection with non-deflected light.

In a case of using a CCD sensor or the like for spectral detection, because the CCD sensor needs to charge light for a length of time, the rotational speed of the spatially partial mirror 0800 needs to be in synchronization with the charging time.

Figure 9A:
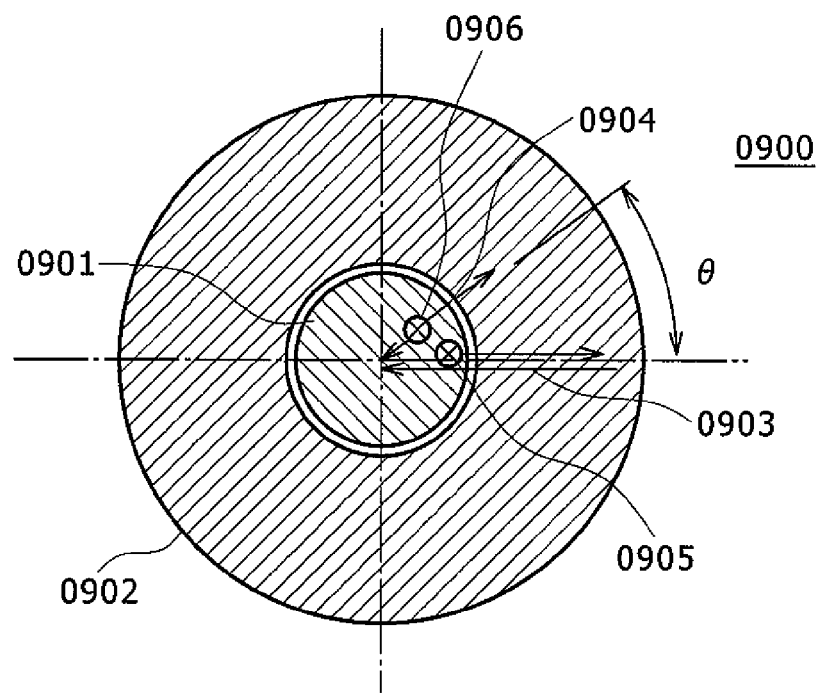
FIG. 9A is a plan view and FIG. 9B is a front view illustrating an example of a reflecting objective.
Figure 9B:
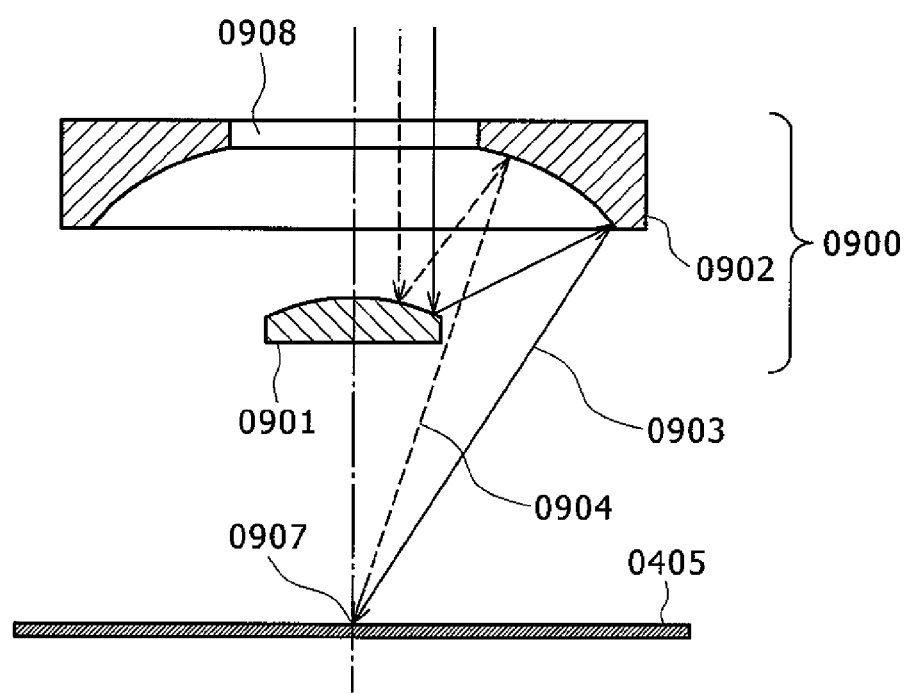

FIGS. 9A and 9B show a reflecting objective 0900 as an example of the objective 0404 in the spectral detection optical system 0400 in FIG. 4. FIGS. 9A and 9B also show the position of the light, which has been emitted from the light source 0401, reflected and deflected by the half mirror 0402, passed through the polarizing element 0403 and entered the reflecting objective 0900, within the pupil of the objective and the relationship between the incident angle and the incident direction of the light traveling to the sample surface. FIG. 9A illustrates the reflecting objective 0900 viewed from above in the optical axis direction, while FIG. 9B illustrates the reflecting objective 0900 viewed from the side. The light entering the reflecting objective 0900 is reflected by a first mirror 0901 and a second mirror 0902 in this order, and focused on the sample surface 0405.

In FIG. 9A, an optical path depicted by a solid line 0903 indicates that light incident upon a pupil face 0905 from the polarizing element 0403 (vertical line in the drawing) is reflected by the first mirror 0901 (rightward line in the drawing) and then is reflected by the second mirror 0902 (leftward line in the drawing) and travels toward a focal point 0907. On the other hand, an optical path depicted by a dotted line 0904 in FIG. 9A indicates that light incident upon a pupil face 0906 from the polarizing element 0403 travels toward the focal point 0907 from a direction inclined θ degree. This indicates that the incident direction in which the light strikes the sample varies depending on which position on the pupil the light strikes. In other words, the position on the pupil which the light strikes determines the incident direction of the light toward the sample surface.

The optical paths represented by the solid line 0903 and dotted line 0904 in FIG. 9B apparently show that the light beams enter the focal point at different incident angles (elevation angle and azimuth angle).

This indicates that the elevation angle and azimuth angle vary depending on the position on the pupil which the light strikes.

Using data of spectral reflectances of the sample surfaces obtained in the above-described way, it is possible to obtain the shape of the pattern formed on the sample surface with the aforementioned scatterometry technique, and to detect defective and non-defective patterns, in short defects, with a threshold.

According to Embodiment 1, the combination of the spatially partial mirror and reflecting objective allows the use of illumination light in a wavelength range from deep ultraviolet to near infrared without chromatic aberration issues and realizes an efficient optical system, resulting in a relatively inexpensive inspection apparatus for detecting defects of minute pattern structures.

Embodiment 2

For detecting the shape of the pattern on a test object with the above-described scatterometry, limiting the angle and direction of light toward and from the sample surface simplifies light phenomenon and therefore makes it easier for subsequent analysis. In addition, applying and detecting light that travels at a specific angle and in a specific direction improves detection sensitivity.

In order to limit the angle and direction of light, a spectral detection optical system according to Embodiment 2, which includes the same components as the spectral detection optical system 0400 in FIG. 4, is provided with a reflecting objective having an aperture stop at the lens pupil for limiting its aperture, instead of the reflecting objective 0900 in FIG. 9 used as the objective 0404. This spectral detection optical system therefore can limit the angle of direction of the light irradiating the sample surface and being detected.

In a case of a finite optical system, the objective 0404 can be considered as a single lens, which means the pupil of the objective 0404 is regarded as being located inside the lens. In a case of the reflecting objective 0900, the pupil is regarded as being located at a space between the first mirror 0901 and second mirror 0902.

Figure 10A:
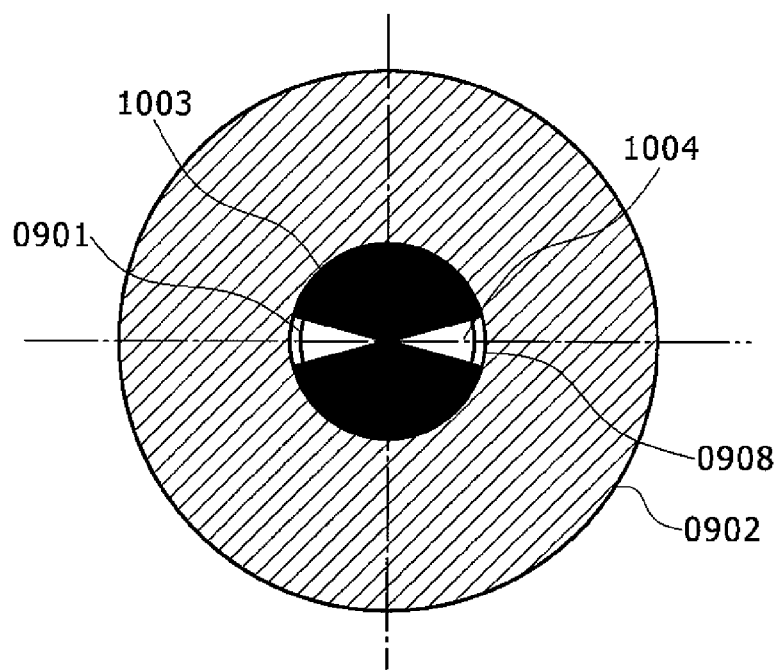
FIG. 10A is a plan view and FIG. 10B is a front view illustrating another example of the reflecting objective.
Figure 10B:
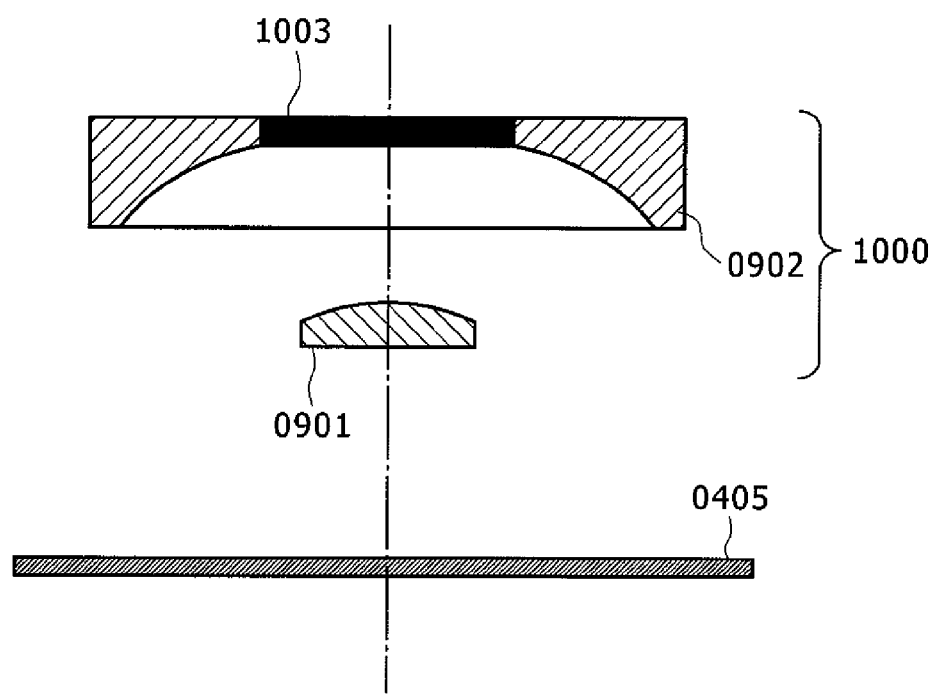

It is preferable to provide an aperture stop at the space between the first mirror 0901 and second mirror 0902; however, adding the aperture stop in a later process is difficult. FIG. 10A shows, as an example, an aperture stop 1003 provided in the aperture 0908 of the second mirror 0902 located above the first mirror 0901 of the reflecting objective 0900 in FIG. 9. Light passes through sub-apertures 1004 of the aperture stop 1003 as shown in FIG. 10B and is irradiated through the reflecting objective 0900 onto the sample surface 0405. Such an aperture stop can be installed later and readily replaced. This aperture stop provides the same effect as an aperture stop located between the first mirror 0901 and second mirror 0902.

The sub-apertures of the aperture stop in FIG. 10A have the shape of a sector, which is an approach for limiting the direction of the light to be irradiated and detected.

Figure 11:
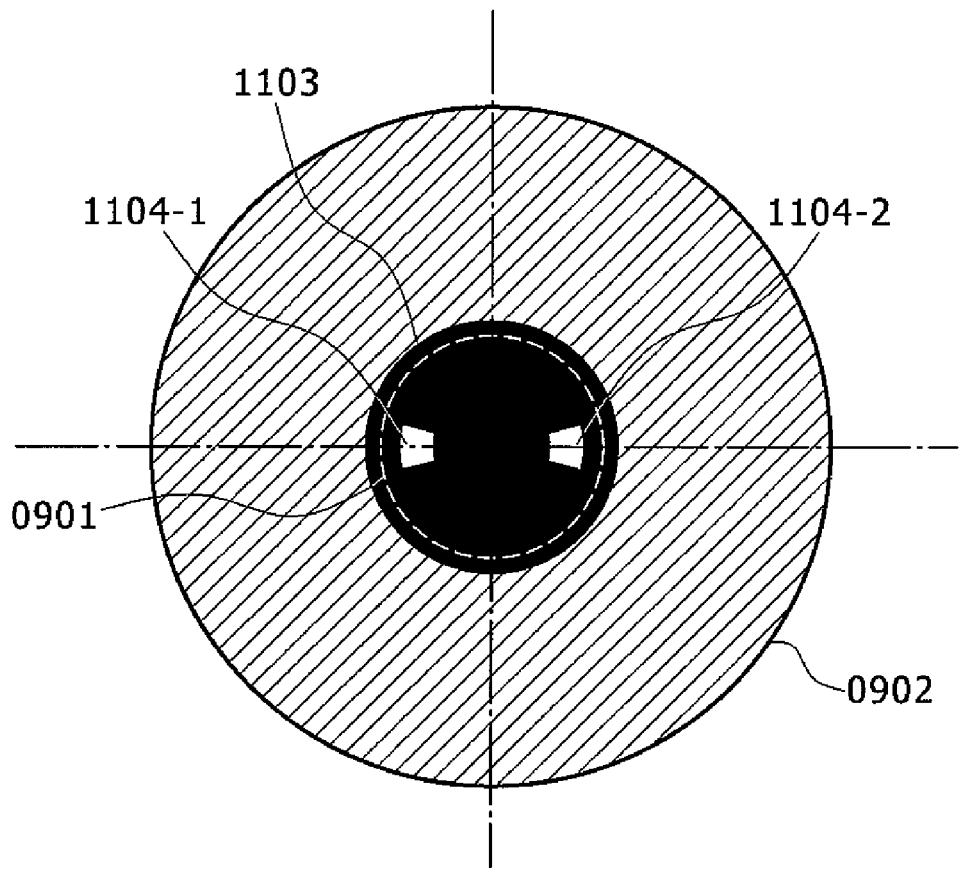
FIG. 11 is a plan view illustrating an example of an aperture stop shape.

FIG. 11 shows another aperture stop 1103 having two sub-apertures 1104-1 and 1104-2 whose length are controlled in the radius direction, thereby limiting the angle of the light to be irradiated and detected.

Figure 12:
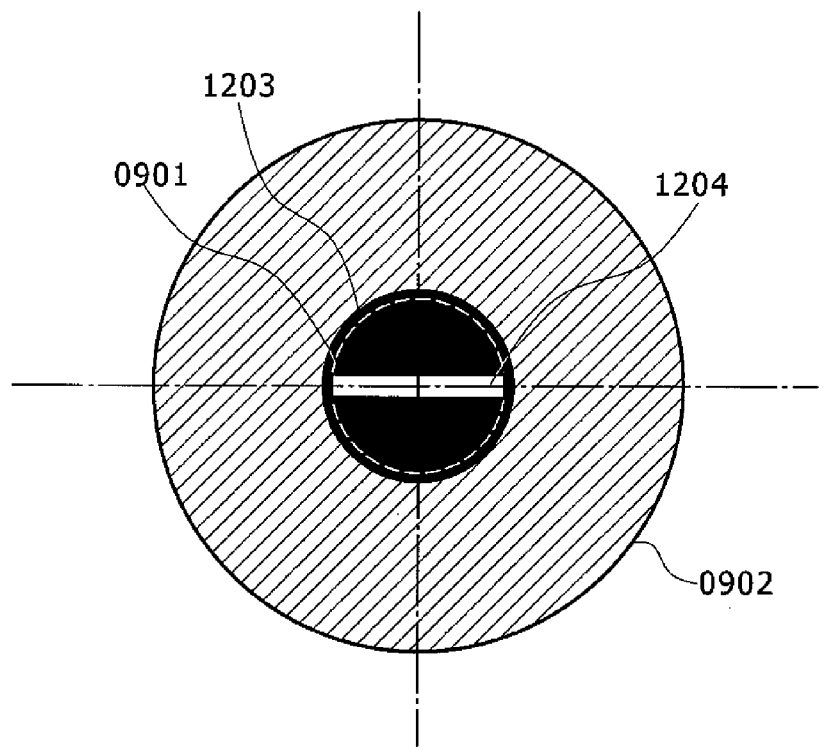
FIG. 12 is a plan view illustrating another example of the aperture stop shape.

FIG. 12 shows an aperture stop 1203 having a slit 1204 as a sub-aperture. The slit 1204 cannot simply limit the range of the angle and direction because the angle range varies according to the direction; however, the slit having a sufficiently small width can provide the same effect as the sub-apertures in FIG. 11.

Figure 13:
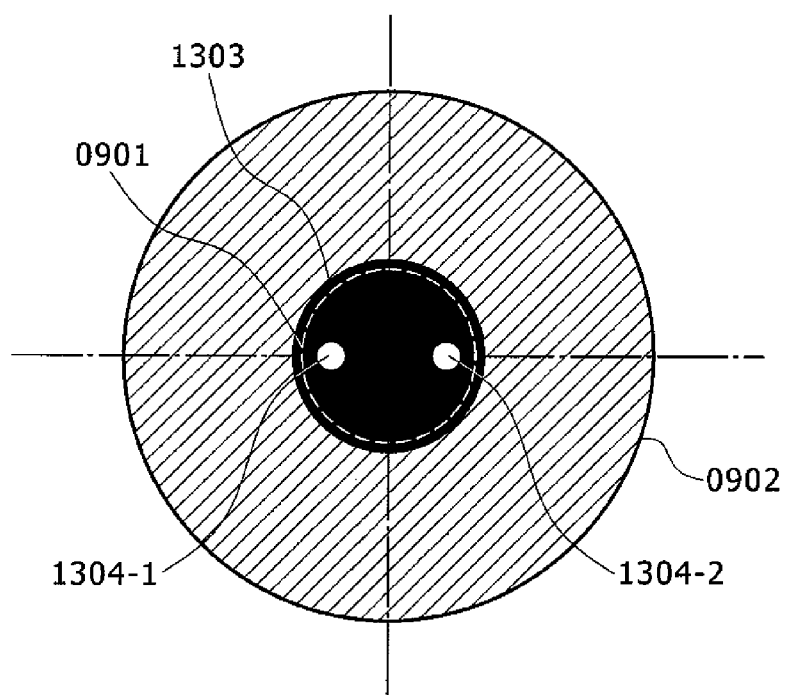
FIG. 13 is a plan view illustrating yet another example of the aperture stop shape.

Furthermore, FIG. 13 shows an aperture stop 1303 having multiple pin holes 1304-1 and 1304-2 as sub-apertures.

In either case, the sub-aperture or sub-apertures are preferably shaped so as to be point-symmetric with respect to the optical axis, because illumination light having passed through one sub-aperture is reflected by the sample and can pass through the other sub-aperture.

As described above, limiting the angle and direction may improve detection sensitivity; however, the optimal conditions vary according to the object to be tested. To obtain the optimal conditions, an adjustable aperture can be applied rather than a fixed one, and the aperture can be adjusted to choose the optimal conditions for each test object.

The methods for adjusting the aperture shape include replacement with a fixed aperture stop and installation of an adjustable aperture stop.

Upon using the combination of the spatially partial mirror functioning as a half mirror and the aperture stop for limiting the angle and direction of irradiation light and detected light, careful consideration must be given to their relationship. Specifically, the spatially partial mirror and the aperture stop needs to be designed so that the light reflected by the spatially partial mirror passes through the aperture stop and the light reflected by the sample again passes through the aperture stop and the spatially partial mirror. In a spectral detection optical system 0400 in FIG. 4 using a reflecting objective 0900 in FIG. 9 instead of the objective 0404, when the light reflected by the half mirror 0402 passes through the sub-apertures provided in the aperture stop 1003, 1103, 1203 or 1303 as shown in FIGS. 10 to 13, then is reflected by the sample surface 0405 and returned to the half mirror 0402 again after passing through the sub-apertures again, the light passes through the non-mirror sections (e.g., the non-mirror sections 0502 in FIG. 5) of the half mirror 0402.

Alternatively, a deliberately designed shape of the spatially partial mirror can play a role in the aperture stop. In this case, it is desirable to make the distance between the spatially partial mirror and objective as small as possible.

Using data of spectral reflectances of the sample surfaces obtained in the above-described way, it is possible to detect the shape of the pattern formed on the sample surface with the aforementioned scatterometry technique, and to detect defective and non-defective patterns, in short defects, with a threshold.

The optimal conditions for limiting the angle and direction of light to be illuminated and detected in Embodiment 2 vary according to the object to be tested. To obtain the optimal conditions, an adjustable aperture can be applied rather than a fixed one, and the aperture can be adjusted to choose the optimal conditions for each test object. The methods for adjusting the aperture shape include replacement with a fixed aperture stop and installation of an adjustable aperture stop.

According to Embodiment 2, limiting the angle and direction of illumination light and detected light improves detection sensitivity.

Embodiment 3

The descriptions in Embodiments 1 and 2 are, in short, about an optical system capable of spectral detection of light in a wide wavelength range from deep ultraviolet to near infrared by limiting the angle and direction of illumination light and detected light. A simpler optical system is shown in FIG. 14 as Embodiment 3

Figure 14:
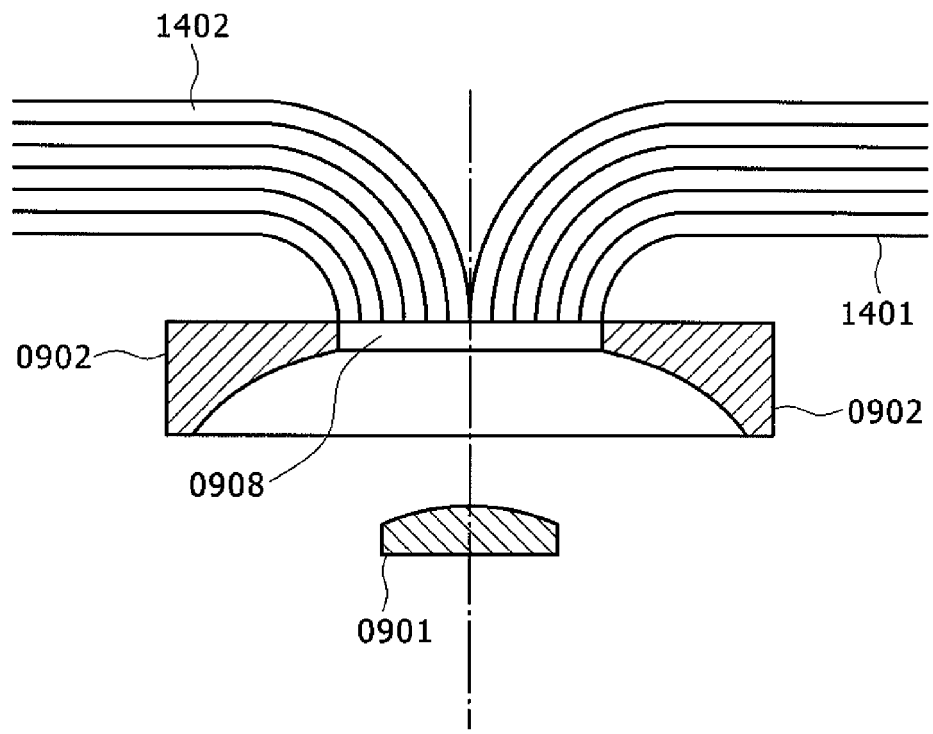
FIG. 14 is a front view illustrating an example of an optical system according to Embodiment 3.

In FIG. 14, optical fibers are directly placed on the aperture 0908 of the second mirror 0902 of the reflecting objective 0900. The optical fibers are divided into illumination fibers 1401 and detection fibers 1402 (fiber bundles), which eliminates the necessity for the half mirror. In addition, the appropriately arranged fibers can obtain the same function as that of the aperture stop. The fibers may be arranged within the pupil in the same way as the aforementioned aperture stop.

Embodiment 4

Figure 15:
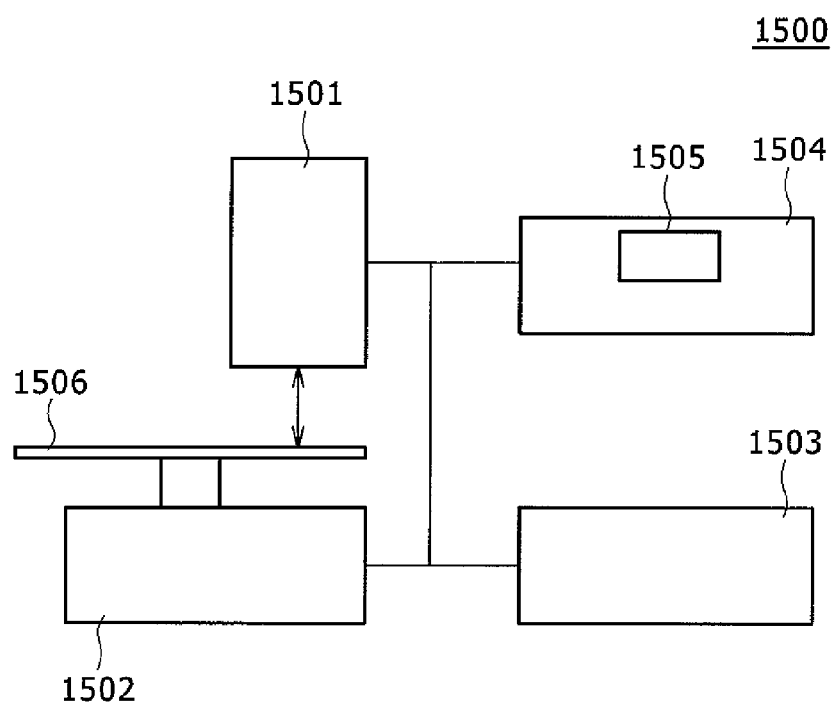
FIG. 15 is a block diagram illustrating the basic structure of a defect inspection apparatus according to Embodiment 4.

FIG. 15 shows an example in which the spectral detection optical system 0400 described in Embodiments 1 to 3 is applied to a hard disk inspection apparatus 1500. The hard disk inspection apparatus 1500 includes a spectral detection optical system 1501 having any one of the structures described in Embodiments 1 to 3, a stage 1502 on which a hard disk medium 1506, which is a test object, is placed and held, the stage 1502 being movable with respect to the spectral detection optical system 1501 so that the spectral detection optical system can perform spectral detection of the hard disk medium 1506 at any position, a data processor 1504 detecting shape defects or shape anomalies of the pattern formed on the hard disk medium 1506 based on the spectral detection results, and a stage controller 1503. The data processor 1504 is provided with a display 1505.

The stage 1502 is movable within a plane parallel with the surface of the hard disk medium 1506 placed on and held by the stage, and also movable in the direction perpendicular to the surface of the hard disk medium 1506 with a mechanism (not shown). In addition, the stage 1502 is configured to rotate the hard disk medium 1506.

Figure 17:
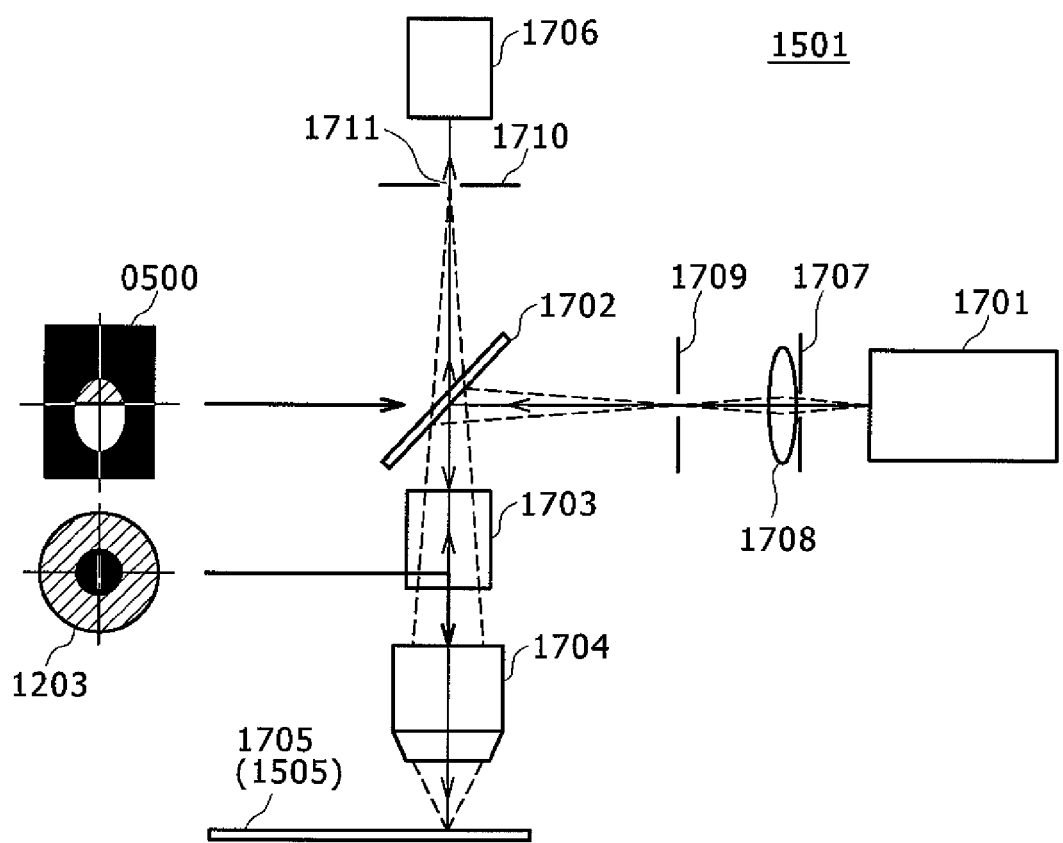
FIG. 17 is a front view illustrating the basic structure of a spectral detection optical system in the defect inspection apparatus according to Embodiment 4.

The spectral detection optical system 1501 has the structure as shown in FIG. 17. The components of the spectral detection optical system 1501 of FIG. 17 are in principle the same as those of the spectral detection optical system 0400 illustrated in FIG. 4; however, a half mirror 0500 shown in FIG. 5, whose ellipse is divided by a straight line lying over a focal point of the ellipse into a light-reflecting section and a light-transmitting section, is employed as the half mirror 0402 in FIG. 4, and an aperture stop 1203 in FIG. 12 is employed as the objective 0404 in FIG. 4 instead of the aperture stop 1003 in FIG. 10. The present embodiment is not limited to the structure, and it is possible to choose a combination of the half mirror 0402 and aperture stop 1003 from the half mirrors in FIGS. 5 to 8 and aperture stops in FIGS. 11 to 13 in various ways to meet inspection conditions.

The spectral detection optical system 1501 in FIG. 17 includes a first diaphragm 1707 having an aperture, a condenser lens 1708, a second diaphragm 1709 having an aperture, a half mirror 1702, a polarizing element 1703, an objective 1704, a third diaphragm 1710 having an aperture and spectral detector 1706. The objective 1704 is specifically a reflecting objective 0900 or 1000 as shown in FIG. 9 or FIG. 10.

Next, the structure of the spectral detection optical system 1501 shown in FIG. 17 will be described. Light with a wavelength component in an ultraviolet range is emitted from the light source 1701, passes through the first diaphragm 1707, condenser lens 1708 and second diaphragm 1709, is reflected by the half mirror 1702 to change its optical path, passes through the polarizing element 1703 and objective 1704 (reflecting objective 0900 or 1000), and is irradiated onto the hard disk medium 1705 (same as the hard disk medium 1506 in FIG. 15) as a test object. The reflected light from the hard disk medium 1705 passes through the objective 1704 and polarizing element 1703 again and is introduced to the spectral detector 1706 after passing through the aperture 1711 of the third diaphragm 1710.

If the aperture 1711 of the third diaphragm 1710 is arranged so as to be located on an imaging position of the objective 1704 (reflecting objective 0900 or 1000), the shape of the aperture 1711 can limit an area on the hard disk medium 1705, more specifically, an area to be tested through the spectral detection by the spectral detector 1706. For example, if the size of the aperture 1711 of the third diaphragm 1710 is set to $\phi 200$ μm and magnification on an imaging surface is twenty times, the spectral detection area on the hard disk medium 1705 is $\phi 10$ μm.

As described above, the use of light having a wavelength of approximately 200 nm limits the applicable optical elements. A xenon lamp, deuterium lamp or other lamps emitting light having a wavelength of 200 nm or more can be used for the light source 1701. However, even light having a wavelength of approximately 400 nm or more can sometimes deliver excellent performance for some test objects. In that case, a halogen lamp or the like, which emits visible light and infrared light, is applicable as the light source.

The optical system according to Embodiment 4 uses a reflecting objective for the objective 1704. In refractive objectives made of general lenses, there are few lenses capable of handling light in a wavelength range from around 200 nm to visible light. On the other hand, reflecting objectives made of mirrors can be used for light with a wavelength of approximately 200 nm or more.

For the spectral detector 1706, there are some commercial spectroscopes adaptable for light of around 200 nm, which are available from Carl Zeiss, Inc., Hamamatsu Photonics K.K., and other companies.

Figure 18:
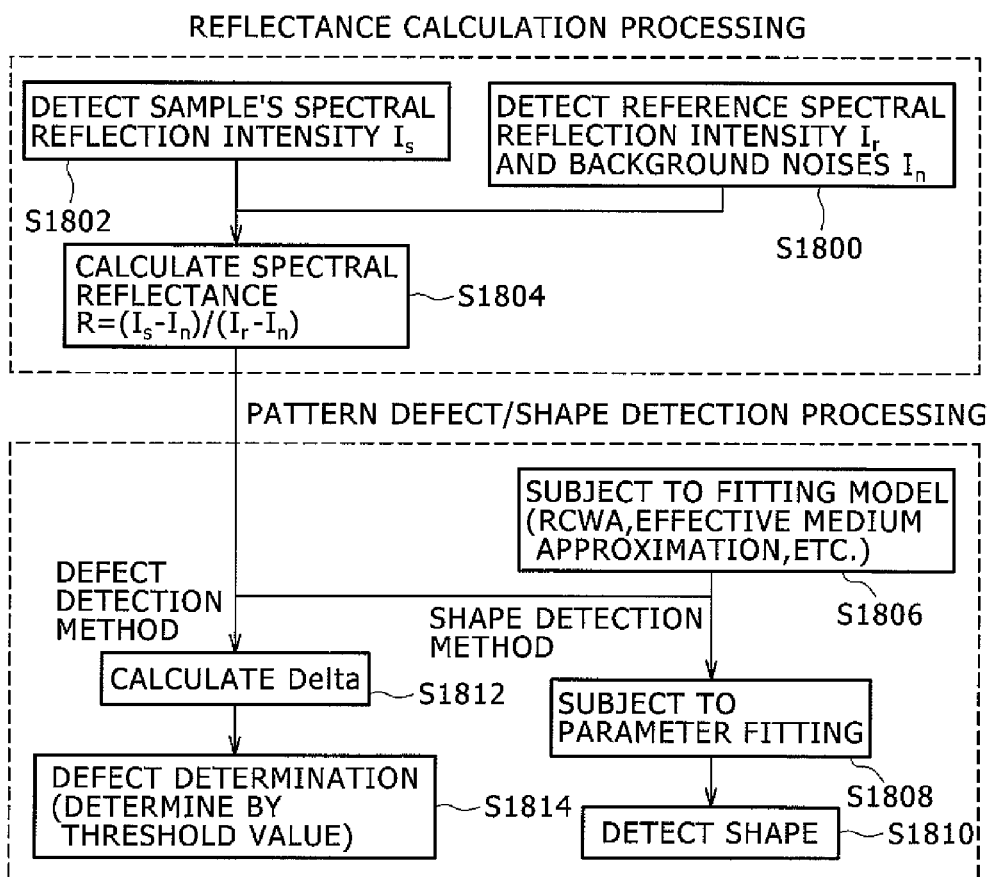
FIG. 18 is a flow chart illustrating processes performed by a data processor.

As shown in FIG. 18, the data processor 1504 executes mainly the following two jobs. One is calculation of reflectance, the other is detection processing of the pattern's shape and defects. As described above, the inspection apparatus according to the present invention detects the shape and defects of the pattern on a test object based on the spectral reflectance of the test object surface. However, the above-described optical system can detect only spectral reflection intensity distributions of the test object surface.

Therefore, as shown by the flow chart in FIG. 18, the inspection apparatus detects the spectral reflection intensity distributions of the mirror-finished surface of a hard disk medium 1705 in advance (S1800), and then obtains the ratio of the spectral reflection intensity of the test object surface to the previously detected spectral reflection intensity (S1802), namely, relative reflectance (S1804). Upon obtaining the relative reflectance, some detectors figure out the spectral reflection intensity data $I_s$ with background noise $I_n$ superimposed thereon. The presence of the background noise $I_n$ should be detected in advance and it has to be subtracted before calculation of the relative reflectance. With the relative spectral reflectance obtained in S1804, the aforementioned pattern shape detection processing (S1806, S1808, S1810) and pattern defect detection processing (S1812, S1814) are executed to detect the shape and defects of the pattern. Although FIG. 18 shows both the defect detection and shape detection, the detection processing to be executed may be only one of these on an as needed basis.

Figure 19:
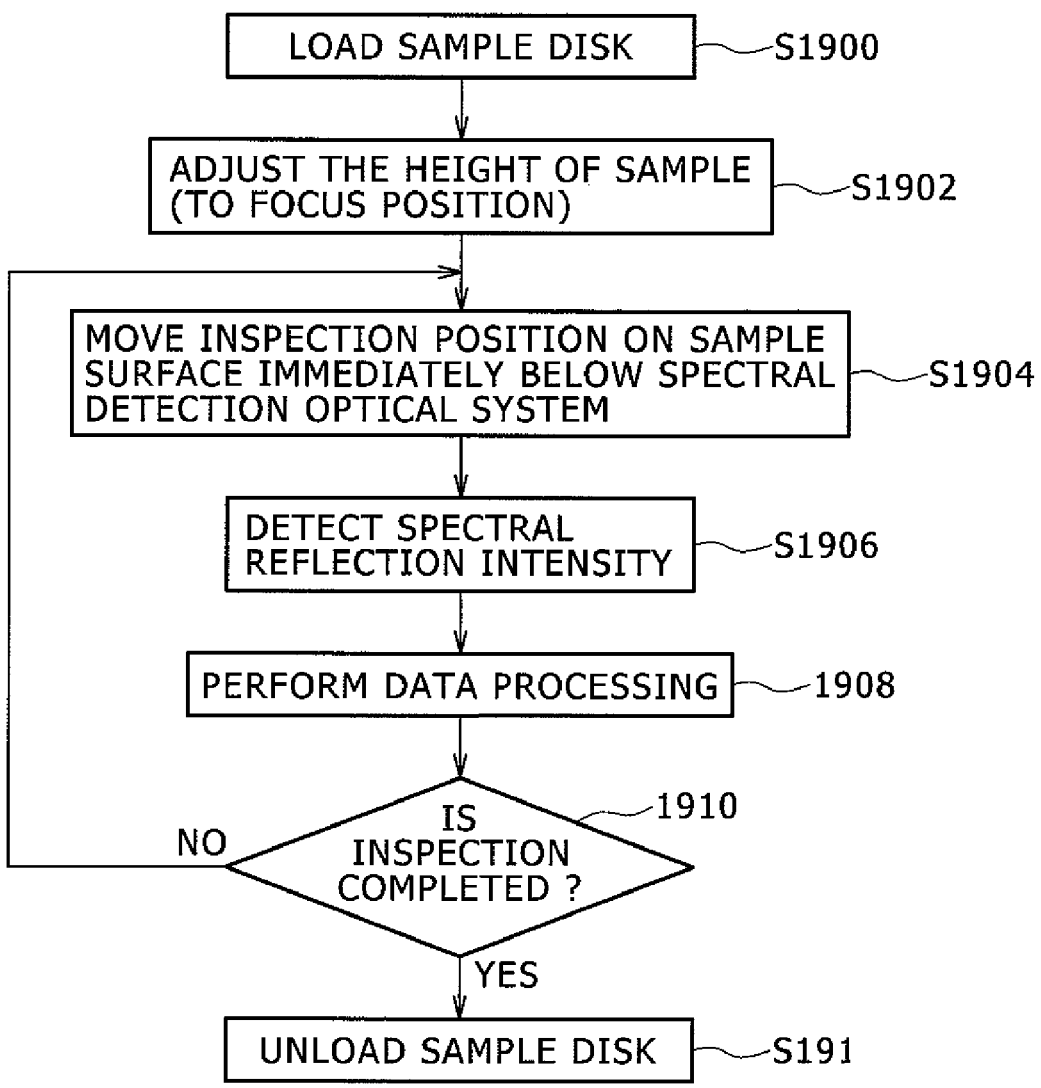
FIG. 19 is a flow chart illustrating inspection processes performed by the defect inspection apparatus.

Referring to FIG. 19, operations of the inspection apparatus will be described. First, a hard disk medium 1506, which is a test object whose center and direction are previously detected (alignment) in the case of necessity, is placed on a stage 1502 (S1900). Next, the hard disk medium 1506, or a test object, is moved to the focus position of the spectral detection optical system 1501 by controlling the height of the stage 1502 through the stage controller 1503 (S1902). Subsequently, the hard disk medium 1506 is controlled by the stage controller 1503 so as to move the inspection area immediately below the spectral detection optical system 1501 (S1904). Then, the spectral reflection intensity of the surface of the hard disk medium 1506 is detected (S1906), and the data processor 1504 detects the shape and defects of the pattern (S1908).

The movement of the stage, spectral detection and data processing are repeated. After the inspection has been completed (S1910), the test disk is removed (S1912). The inspection results are indicated on the display 1505. Descriptions about the alignment of the hard disk medium 1506, or the test object, and the placement and removal operations of the media to and from the stage 1502 will be omitted.

If the entire surface of the hard disk medium 1506 is inspected after continuous operations of the stage movement, spectral detection and data processing from S1904 to S1908, the spiral area on the disk can also be inspected.

The above-described inspection makes it possible to detect the shape and defect distributions of the pattern formed on, for example, the patterned medium 1506.

Although the aforementioned embodiments are examples of defect detection of patterns on hard disk media, the present invention is not limited to the embodiments, various modifications and alterations may occur without departing from the true spirit and scope of the invention as defined in the appended claims.

What is claimed is:

1. A spectral detection optical system comprising:
   a light source emitting light in a wavelength range including ultraviolet;
   an optical path switching unit including a light-transmitting section and a light-reflecting section, the optical path switching unit switching an optical path of the light emitted from the light source by reflecting the light with the light-reflecting section;
   a reflecting objective unit focusing the light whose optical path has been switched by the optical path switching unit onto a surface of a sample; and
   a spectral detection unit subjecting reflected light to spectral detection, the reflected light being the light that is applied onto the surface of the sample by the reflecting objective unit, is reflected by the sample surface, passes through the reflecting objective unit and the light-transmitting section of the optical path switching unit.

2. The spectral detection optical system according to claim 1, wherein
   the reflecting objective unit includes an aperture in the vicinity of a pupil of the reflecting objective unit, the aperture allowing the light emitted from the light source to partially pass therethrough to apply the light onto the sample from a desired direction.

3. The spectral detection optical system according to claim 1, wherein
   the light-transmitting section and the light-reflecting section of the optical path switching unit are located in an ellipse area.

4. A defect inspection apparatus comprising:
   a stage unit on which a sample is placed;
   a spectral detection optical unit subjecting reflected light to spectral detection, the reflected light being light that is applied to the sample on the stage unit and is reflected by the sample;
   a data processing unit detecting the shape and defects of the sample on the stage unit based on results of the spectral detection performed by the spectral detection optical unit; and
   a stage control unit controlling the movement of the stage unit, wherein
   the spectral detection optical unit includes a light source emitting light in a wavelength range including ultraviolet, an optical path switcher having a light-transmitting section and a light-reflecting section, the optical path switcher switching an optical path of the light emitted from the light source by reflecting the light with the light-reflecting section, a reflecting objective focusing the light whose optical path has been switched by the optical path switcher onto a surface of the sample, and a spectral detector subjecting reflected light to spectral detection, the reflected light being the light that is applied onto the surface of the sample by the reflecting objective, is reflected by the sample surface, passes through the reflecting objective and the light-transmitting section of the optical path switcher.

5. The defect inspection apparatus according to claim 4, wherein
   the reflecting objective in the spectral detection optical unit includes an aperture in the vicinity of a pupil of the reflecting objective, the aperture allowing the light emitted from the light source to partially pass therethrough to apply the light onto the sample from a desired direction.

6. The defect inspection apparatus according to claim 4, wherein
   the light-transmitting section and the light-reflecting section of the optical path switcher in the spectral detection optical unit are located in an ellipse area.

7. A spectral detection method comprising the steps of:
   emitting light in a wavelength range including ultraviolet by a light source;
   switching an optical path of the light by reflecting the light with a light-reflecting section of an optical path switching unit to direct the light to a reflecting objective unit;
   focusing the light, which has entered the reflecting objective unit, onto a surface of a sample; and
   subjecting reflected light to spectral detection, the reflected light being the light that is applied onto the sample, is reflected by the sample surface, passes through the reflecting objective unit and a light-transmitting section of the optical path switching unit.

8. The spectral detection method according to claim 7, wherein
the light whose optical path has been switched by the optical path switching unit partially passes through an aperture located in the vicinity of a pupil of the reflecting objective unit and then enters the reflecting objective unit.

9. The spectral detection method according to claim 8, wherein
the light emitted from the light source is reflected by the light-reflecting section located in a part of an ellipse area provided in the optical path switching unit to direct the light to the reflecting objective unit, and the reflected light, which is reflected by the sample and focused by the reflecting objective unit, passes through the light-transmitting section located in a part of the ellipse area provided in the optical path switching unit to be subjected to the spectral detection.

10. A defect inspection method for performing spectral detection for light applied onto a sample placed on a stage unit and then reflected by the sample to detect defects of the sample based on results of the spectral detection, the method comprising the steps of:
irradiating the sample placed on the stage with light;
subjecting reflected light to spectral detection, the reflected light being the light in a wavelength range including ultraviolet emitted from a light source, an optical path of the light being switched by reflecting the light with a light-reflecting section of an optical path switching unit to enter a reflecting objective unit that focuses the light on a surface of the sample, the light applied onto the sample being reflected by the sample; and
subjecting reflected light to spectral detection, the reflected light being the light applied to and reflected by the sample, passes through the reflecting objective unit and a light-transmitting section of the optical path switching unit.

11. The defect inspection method according to claim 10, wherein
the light whose optical path has been switched by the optical path switching unit partially passes through an aperture located in the vicinity of a pupil of the reflecting objective unit and then enters the reflecting objective unit.

12. The defect inspection method according to claim 10, wherein
the light emitted from the light source is reflected by the light-reflecting section located in a part of an ellipse area provided in the optical path switching unit to direct the light to the reflecting objective unit, and the reflected light, which is reflected by the sample and focused by the reflecting objective unit, passes through the light-transmitting section located in a part of the ellipse area provided in the optical path switching unit to be subjected to the spectral detection.

* * * * *